United States Patent [19]

Block et al.

[11] Patent Number: 4,716,121
[45] Date of Patent: Dec. 29, 1987

[54] FLUORESCENT ASSAYS, INCLUDING IMMUNOASSAYS, WITH FEATURE OF FLOWING SAMPLE

[75] Inventors: Myron J. Block, North Salem, N.H.; Tomas B. Hirschfeld, Livermore, Calif.

[73] Assignee: Ord, Inc., Nahant, Mass.

[21] Appl. No.: 773,940

[22] Filed: Sep. 9, 1985

[51] Int. Cl.[4] .............. G01N 33/533; G01N 33/552; G01N 21/64; G01N 35/00
[52] U.S. Cl. .................................. 436/514; 250/302; 250/461.1; 356/73.1; 356/445; 422/57; 436/172; 436/501; 436/527; 436/546
[58] Field of Search .............. 436/172, 501, 527, 546, 436/514; 250/302, 461.1; 422/57; 356/73.1, 445

[56] References Cited

U.S. PATENT DOCUMENTS

| | | | |
|---|---|---|---|
| 4,153,675 | 5/1979 | Kleinerman | 436/805 X |
| 4,293,310 | 10/1981 | Weber | 436/805 X |
| 4,297,273 | 10/1981 | Buckler | 436/805 X |
| 4,398,894 | 8/1983 | Yamamoto | 436/805 X |
| 4,436,827 | 3/1984 | Tamagawa | 436/805 X |
| 4,447,546 | 3/1984 | Hirschfeld | 436/805 X |
| 4,558,014 | 12/1985 | Hirschfeld | 436/805 X |
| 4,582,809 | 4/1986 | Block | 436/805 X |
| 4,671,938 | 6/1987 | Cook | 356/445 X |

Primary Examiner—Sidney Marantz
Attorney, Agent, or Firm—Schiller, Pandiscio & Kusmer

[57] ABSTRACT

An assay method and apparatus employing total internal reflection of excitation radiation at an activated region on the surface of an optically conductive rod or fiber surrounded by a liquid phase of lower index of refraction, so as to excite into fluorescence fluorophores in the liquid present in a thin layer around the rod surface. The induced fluorescence is then gathered and measured. Excitation occurs while flowing a sample of the liquid phase through an enclosure of fixed dimensions bounded in part by the activated region.

11 Claims, 3 Drawing Figures

FLUORESCENT ASSAYS, INCLUDING IMMUNOASSAYS, WITH FEATURE OF FLOWING SAMPLE

This invention relates to immunoassay, and more particularly to fluorescent immunoassay wherein the evanescent wave produced by total internal reflection is used to restrict the observed volume to a lamina, thereby avoiding a separation or wash step while also reducing the effects of interfering, immunologically non-reacting background substances in the sample.

The use of total internal reflection techniques to reduce the effects of immunologically non-reactive substances in immunoassays has been the subject of a number of investigations. For instance, in U.S. Pat. No. 3,939,350, the evanescent wave produced by total internal reflection at the interface between a totally internally relecting substrate, such as a plate, and the sample is used to induce fluorescence in a fluorescently tagged portion of the sample immunologically bound to the plate, the portion of the sample beyond the evanescent zone not being excited. In this way, an assay may be performed without the necessity of removing the unreacted sample and reagent. In effect, the evanescent wave functions as a separation mechanism.

As taught in U.S. application Ser. No. 406,324, filed Aug. 9, 1982, U.S. Pat. No. 4,582,809, and assigned to the assignee of the present application, greater optical efficiency may be achieved by observing the fluorescence, excited by the evanescent wave, that reenters (tunnels back into) the optically denser medium and propagates therein by total internal reflection. An improved apparatus of this type and the corresponding method of immunoassay is taught in U.S. Pat. No. 4,447,546, where it is shown that both the amount of sample and the reaction end point may be automatically controlled by surrounding a controlled area of the immunologically activated totally reflecting element (e.g. a known length of an optical fiber of known diameter) with a capillary tube of known dimensions. In this manner, rapid, simple, and accurate non-ballistic assays may be performed.

The measurement time required for incubation in the capillary surrounded fiber apparatus is proportional to the square of the mean diffusion distance. The latter is of the order of the distance between the fiber and the capillary wall. By making this distance smaller, the time required to reach the reaction end point, and hence the speed of a non-ballistic assay may be dramatically improved. However, such a reduction also reduces the sampled volume and thus the total signal per unit length of fiber, and thus deleteriously affects sensitivity. Such loss of sensitivity can only be partially regained by increasing the fiber length due to signal attentuation in an unclad fiber, as required by the present invention.

Accordingly, it is an object of the present invention to provide apparatus and methods for a more rapid, enclosed-fiber, fluorescent immunoassay wherein the sensitivity of the assay is not deleteriously affected by the increased speed.

It is another object of the present invention to provide apparatus and methods for an increased sensitivity fluorescent immunoassay.

These and other objects are met in the present invention of a total internal reflection fluorescence immunoassay wherein the sample is caused to flow along the length of a totally internally reflecting substrate having an active surface region surrounded by and spaced from an enclosure to provide a fixed volume, the sample flow rate being adjusted to make the dwell time of the sample opposite the active region similar to the time required to scavenge the volume between the substrate and enclosure. In a preferred embodiment, the substrate is an optical fiber and the enclosure is a tube dimensioned and disposed so that the distance between the internal wall of the tube and the fiber surface is of capillary dimensions.

With this structure, a large sample volume may be sampled in relatively short time, with but a small part of the sample being illuminated by the evanescent wave at any one time. The binding to the activated portion of the fiber is cumulative, depending on the titre of the unknown in the sample and the volume scavenged.

Other objects of the invention will in part be obvious and will in part appear hereinafter. The invention accordingly comprisies the apparatus possessing the construction, combination of elements, and arrangement of parts and the method comprising the several steps and the relation of one or more of such steps with respect to each of the others which are exemplified in the following detailed disclosure and the scope of the application of which will be indicated in the claims.

BRIEF DESCRIPTION OF THE DRAWINGS

For a fuller understanding of the nature and objects of the present invention, reference should be to the following detailed description taken in connection with the accompanying drawings wherein.

In the figures, like index numbers refer to like elements. It should also be noted that the representation in the figures is diagrammatic and no attempt has been made to indicate actual scales or ratios.

Figure 1:
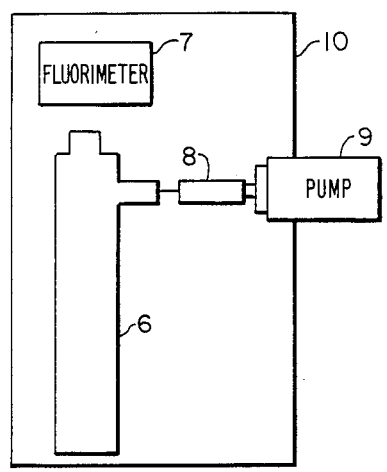
FIG. 1 is a diagrammatic representation of the apparatus of the present invention as connected to known apparatus for the purpose of this invention.

With reference to terminology, it will be noted in the detailed description of the apparatus of this invention that portions of the apparatus are referred to as "upper" and "lower" portions. This is done wholly for convenience and to relate the description to the diagramatic representations in the drawings. It will be appreciated that the apparatus can function in any position or orientation and it is within the scope of this invention to have it do so.

The present invention operates by total reflection fluorescence, coupled with tunneling of the radiation, as described in copending U.S. application Ser. No. 406,324, filed Aug. 9, 1982, and assigned to the assignee of the present application, and which is incorporated herein by reference for further details particularly of the optical mode of operation of the apparatus.

FIG. 1 illustrates exemplary apparatus useful to practice of the present invention, which apparatus comprises kit 6, fluorometer 7, syringe 8, syringe pump 9, and container 10.

Figure 2:
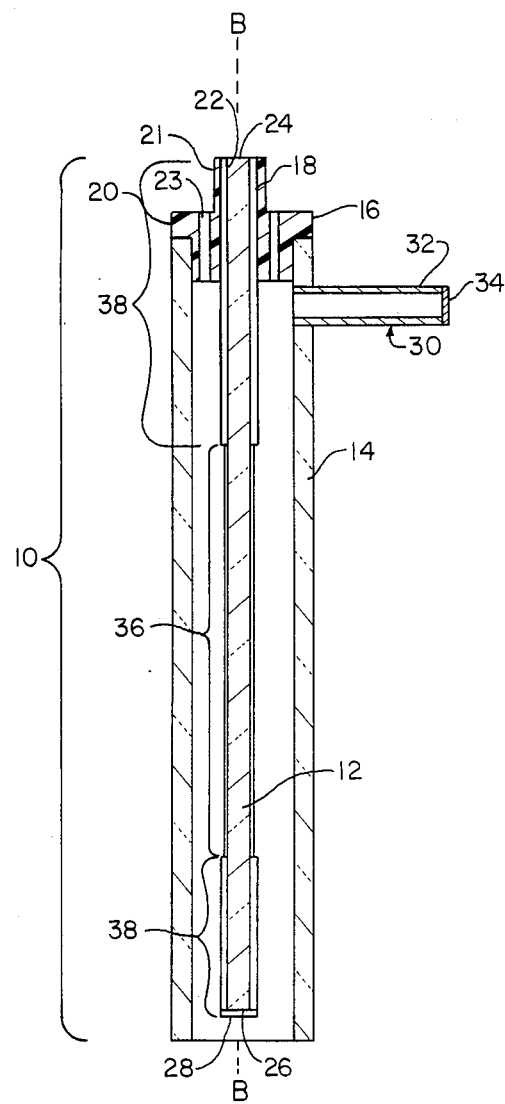
FIG. 2 is longitudinal cross-sectional view of a immunoassy kit which forms a preferred embodiment of a portion of the apparatus of the present invention.

Referring to FIG. 2, there may be seen a longitudinal cross-sectional view of an immunoassay kit 6 made in accordance with the principles of the present invention.

Kit 6 comprises optical fiber 12, capillary tube 14, and stopper 16.

Fiber 12 is an elongate substantially cylindrical optically transparent body adapted to propagate along its length by multiple total internal reflections, optical radiation entering an end of the fiber within an established solid angle substantially rotationally symmetric about the fiber's axis. As is well known in the art of fiber optics, the maximum acceptance angle, with regard to the fiber axis, B, for the radiation entering the fiber and so propagated within it, is established by the refractive indices of the fiber and the surrounding medium. For radiation initially propagating through a medium of refractive index no , incident upon a fiber of refractive index $n_1$ otherwise surrounded by a material of refractive index $n_2$, the maximum acceptance angle may be found from the equation $$N.A. = n_0 \sin B = (n_1^2 - n_2^2)^{\frac{1}{2}} \quad (1)$$

where N.A. is the so-called numerical aperture of the fiber. By way of example, but not limitation, fiber 12 may be any of a number of optically transparent materials, such as glass, quartz, polypropylene, polyolefin, nylon, or the like, chosen to have an index of refraction greater than that of the fluid sample being assayed. The latter typically is an aqueous solution having an index of refraction near 1.33 or a serum sample having an index of refraction near 1.35. The fiber is further chosen of a material that is relatively insoluble and non-reactive with the fluid sample. It has been found that 200 microns is a satisfactory fiber diameter, although other fiber diameters may be used. For most assays, a fiber 25 mm in length appears adequate; however, it will be understood that the length of the fiber can be accommodated to the assay to be undertaken. Sensitivity in fact improves with increase in fiber length until signal attenuation over the fiber length exceeds 1/e.

As will be described in detail hereinafter, fiber 12 is provided with a surface coating including means for attaching selected moieties of an antigen-antibody complex. As herein used, the term "antigen-antibody complex" includes complexes not only of complete antibodies and antigens, but complexes incorporating immunologically reactive fragments of either or both.

Capillary tube 14 is preferably an optically transparent tube, its material of construction also being chosen to be relatively insoluble and nonreactive with the fluid sample being assayed. Thus, capillary tube 14 is preferably fabricated from such materials as glass, quartz, polypropylene, polyolefin, or the like. In a preferred embodiment, capillary tube 14 is of right circular cylindrical bore, having an inside diameter a slightly larger than the diameter of fiber 12 (e.g., for a fiber diameter of 200 microns, capillary tube 14 may have an inside diameter of about 240 microns). However, as will be described, the invention may be practiced with capillary tubes of considerably greater internal diameter than the fiber.

Stopper 16 is configured and dimensioned to fit within an end of capillary tube 14 and support an end portion 18 of fiber 12 substantially coaxially and in spaced-apart relation within the capillary tube. Additionally, stopper 16 provides a hard locating surface for positioning kit 6 in a fluorimeter as will be described hereinafter. To these ends, stopper 16 is preferably provided with a flange 20 having an overall diameter on the order of the outside diameter of capillary tube 14 and a centrally disposed ferrule-like extension 21 coaxial with a central bore 22. Bore 22 penetrates throughout stopper 16, and is dimensioned to secure end portion 18 of fiber 12. In a preferred embodiment, stopper 16 is molded in place about fiber 12, the stopper being preferably fabricated of a low refractive index material, such as siloxane. Fiber 12 passes through and is supported by stopper 16 so as to expose substantially all of the fiber but end portion 18 to the interior of capillary tube 14, leaving end face 24 of end portion 18 unobscured and coterminous with the extremity of bore 22 external to the capillary tube.

End face 24 is preferably planar and disposed normally to the axis of fiber 12. Preferably, end face 24 is also highly transparent and free of blemishes which would tend to scatter light incident upon the end face. To this end, end face 24 may be optically polished, although it has been found that fused quartz fiber may be cleaved to provide an adequate optical surface.

Optionally, the end face 26 of the fiber distal from end face 24 is also polished flat or cleaved and further provided with a mirror coating 28 (or a separate mirror) disposed substantially normal to the fiber axis, thereby causing radiation trapped in the fiber to double-pass the fiber.

The overall dimensions of fiber 12, capillary tube 14, and stopper 16 preferably are chosen to insure that end face 26 of the fiber is within the capillary tube.

It will be realized that kit 10 as thus described is essentially the same as that taught in U.S. Pat. No. 4,447,546. Importantly however in the present invention, tube 14 is provided with port 30 in fluid communication with the interior of tube 14 distal the open end of the tube. In a preferred embodiment, port 30 is in the form of a tubular conduit 32 provided with a septum 34. Tubular conduit 32 is located proximate stopper 16 and extending radially from tube 14. Septum 34 is adapted, as well known in the art, to be penetrated by a hypodermic needle (not shown), and the interior of conduit 32 is dimensioned to accommodate the needle intended for use with the system. It will be understood that port 30 might equally well be the appropriate coupling for attachment to a Luer lock-equipped syringe, or some equivalent apparatus.

Prior to being assembled into kit 10, fiber 12 is provided a coating, as will be described, activating a region 36 of the cylindrical surface of the fiber for the assay to be performed. In a preferred embodiment, the activated region 36 is restricted to a predetermined length of fiber 12 by a chemically and optically inert coating 38 of, for instance, low optical index silicone, extending over both ends of the fiber. It will be understood, however, that the dimensions of activated region 36 may be controlled by other means (e.g., by masking the fiber during coating), or, alternatively, the entire length of fiber 12 might be activated and the length of the fiber disposed within the capillary tube to be carefully controlled.

Figure 3:
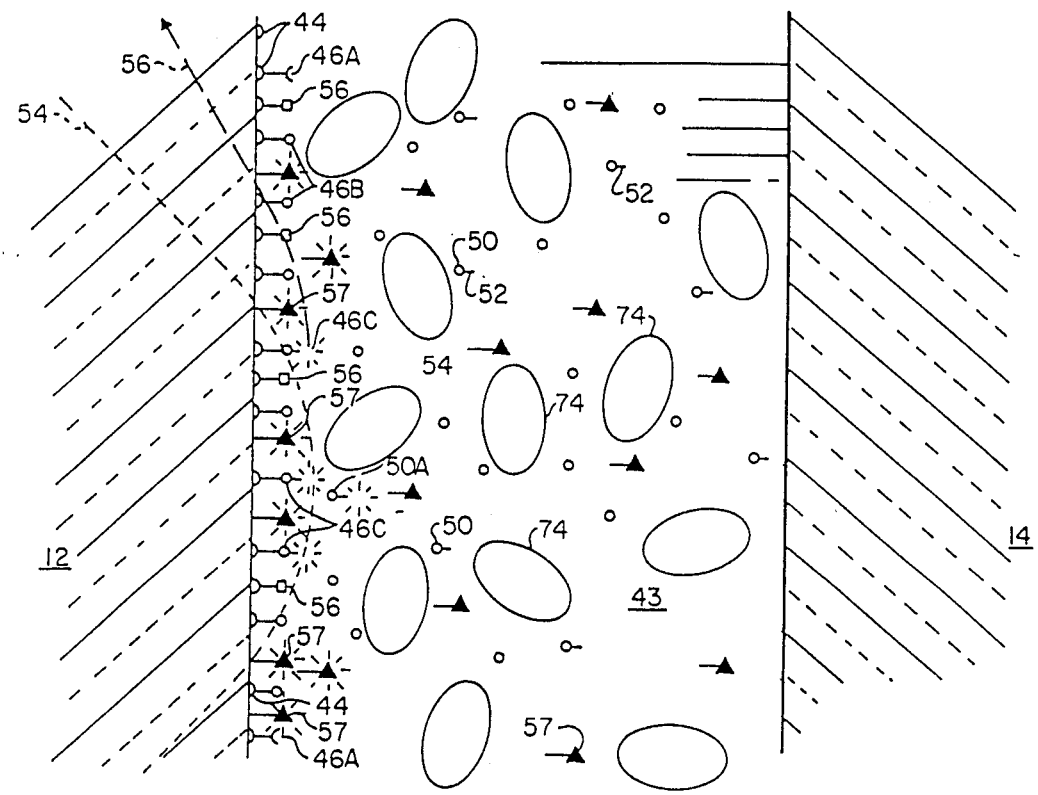
FIG. 3 is a stylized view of a portion of the apparatus of FIG. 2, illustrating a typical immunochemical reaction in the realization of the present invention.

Turning now to FIG. 3, there may be seen a highly stylized representation of a longitudinal crosssectional portion of kit 2 within activated region 36 of fiber 12, filled with a sample 43 to be assayed. The surface of fiber 12 within region 34 is provided with a plurality of coupling sites 44, to a number of which are bound a moiety 46 of the antibody-antigen complex. As used herein, the phrase "moiety of an antibody-antigen complex" refers to an immunologically reactive portion of such a complex, and includes haptens as well as complete antigens and antigen reactive antibody fragments [Fab] as well as complete antibodies. Coupling sites 44 are so selected as to immobilize moieties 46 without appreciably affecting the reactivity (e.g., the affinity and avidity) of the moiety for the complementary portion of the complex. In a preferred embodiment, fiber 12 is of glass or quartz, coupling sites 44 are the reactive groups of a silyl compound such as 3-aminopropyltrimethoxysilane, and moieties 46 are an antibody such as immunoglobulin G (IgG). This particular combination of solid phase, coupling site 44 and moiety 46 may be bound through the antibody's carboxyl terminations, thereby leaving the antibody's antigen reactive amino terminations free.

The methods of preparing the glass surface of fiber 12, of attaching the silyl compound thereto, and of covalently bonding an antibody to the glass through the silyl coupling, are described by Weetall (U.S. Pat. No. 3,652,761), where may also be found a description of other silyl compounds and the methods by which carboxyl, amino, and other reactive groups of antibody or antigen (or their fragments) may be covalently bound to various inorganic materials. It should be noted that an extensive art for immobilizing antigens or antibodies to polymers also exists, and those skilled in the art will understand that coupling sites 44 for antigen or antibody might be provided on polymeric fibers also. Thus, for instance, if fiber 12 is of nylon (polyamide), the coupling may be in the form of the substitution of an appropriate radical for the hydrogen bound to the polymer's amino groups. It should be noted that coupling sites 44 may also incorporate spacer groups, as are well known in the art, to insure sufficient separation between fiber 12 and moieties 46 as to minimize steric hindrance of the antibody-antigen binding process. For example, coupling sites 44 might include a polyethylene chain, as for example in the case of 1,6 diaminohexane or 6 aminohexanoic acid bound to fiber 12 through a peptide bond and respectively providing a free primary amino and a free carboxyl group for covalent binding to the carboxyl or amino termination of a protein moiety 46. Either of these coupling materials provide a 6-carbon chain between terminations, thereby spacing moiety 46 from fiber 12 by the corresponding distance. Similar appropriate coupling and spacer materials are well known in the arts of both immunoassay and affinity chromotography.

In a preferred embodiment, fiber 12 is provided with moiety 46 having occupied binding sites, as indicated at index numerals 46C, the moieties being in part provided with attached tagged complement 50 for competition immunoassays. Thus, in one embodiment moiety 46 is an antibody, and a preloading of tagged antigen or hapten is incorporated into the coating of fiber 12. Each of the tagged components 50 is provided with a predetermined quantity of fluorophore 52, thereby providing a tag. The particular fluorescing compound of interest for tagging include fluorescein, tetramethylrhodamine, rare earth chelates, and the like. Methods for linking fluorescent tags to proteins are well known in the art, and many of the commercially available fluorescing compounds have groups for linking to proteins. Preferably, for competition assay, a fixed portion of coupling sites 44 are provided with a immunologically inert protein 56, such as albumin. The coating can be made to have a fixed surface composition by using absorption phenomena, as follows. For a coating solution prepared with appropriate concentration of the reagents, mere immersion of a fiber activated with the proper surface binding groups 44 will produce a surface monolayer of chemically bound protein. The proportion of, immunoglobulin to inert protein in this layer will be given by (but not identical to) their proportion in the solution. Any partial filling of the immunoglobulin active sites with tagged antigen will, of course, be maintained at the level in the solution. After dipping, the fiber is removed from the coating solution. To prevent the adhering liquid layer from entraining additional reagent, the fiber is then quickly washed before further evaporation can occur. The protein layer, being covalently bound, will not be dislodged by this process. In order to prevent binding of more than one layer of protein, the bifunctional reagent must not alter the net charge of the protein (this can be controlled by adjusting the pH of the coating solution) and not have too long a spacer arm.

Kit 6 is intended for use with fluorimeter 7 (FIG. 4) which is chosen to excite and accept fluorescence from the tagged component of the reagent. A suitable fluorimeter is described in the aforementioned U.S. Pat. No. 4,447,546, wherein may also be found a description of its operation. Importantly, as described in the latter patent, the fluorimeter preferably reads the fluorescent emission propagated back toward that end of the fiber at which the excitation radiation was introduced.

Kit 6 of the present invention is used much as in either of the other patent applications hereinbefore referred to. However, and importantly, in the present invention, the volume of sample used in a determination is not necessarily limited by the interspatial volume between fiber 12 and tube 14.

In use, the preferred embodiment of the apparatus of the present invention requires first that a sample be drawn into syringe 8 which is then connected, as by a Luer lock to kit 10 as in FIG. 1, i.e, syringe 8 is placed in syringe pump 9 and kit 6 is connected to fluorometer 7. Syringe pump 9 is now activated, forcing the sample in syringe 8 through kit 6 at a flow rate as will be described. Pump 9 thus constitutes means for controlling the flow rate so that the dwell time of the sample 43 opposite activated region 36 is similar to the time required to thoroughly scavenge the volume between fiber 12 and tube 14. Faster flow rates will increase the sensitivity of the system but will tend to decrease the efficiency of use of the sample because of incomplete scavenging. The sample flow through the interspace between fiber 12 and tube 14 should completely fill that interspace and preferably keep it filled during the entire assay. As taught in U.S. Pat. No. 4,447,546, fluorimeter 7 is configured so as to illuminate end face 24 of fiber 12 within the cone angle defined by the numerical aperture of the fiber. This radiation is consequently propagated within fiber 12 at or above the critical angle (as indicated by ray 54 in FIG. 3) and multiply totally internally reflected along the length of the fiber. As a result, an evanescent wave is produced in fluid 43 adjacent the fiber during the flow of the sample part activated region 36.

Competitive binding of tagged components 50 and untagged components 54 to moieties 46 attached to the fiber results in fluorescently tagged complexes 46C in proportion to the relative concentration of tagged to untagged components. Excited by the evanescent wave, the tagged complexes 46C fluoresce. A portion of the fluorescent emission tunnels into the fiber, propagating within the fiber along paths exceeding the critical angle, as indicated, for instance, by ray 56 in FIG. 3. One-half or more of this totally reflected fluorescence emission exits the fiber at end face 24, where it is collected by fluorimeter 7.

If the interspace between the fiber and tube is completely filled with sample fluid, at least adjacent activated region 36, the volume of sample instanaeously opposite active region 36 of the fiber is given by $$V = L\, pi\, (D^2 - d^2)/4 \qquad (2)$$

where L is the length of active region 36 of fiber 12, D is the inside diameter of the capillary, and d is the diameter of the fiber. The volume observed is given by a similar relation, with the quantity (D−d) replaced by the effective thickness of the observed zone. The incubation time, necessary to scavenge a static volume as given by equation (2) is $$t = k\, [(D-d)/(2s)]^2 \qquad (3)$$

where k is a dimensionless chemical reaction constant (depending, e.g., on the density of binding sites on the fiber, the probability a reacting species in the sample encounters a binding site, etc.) and s is the Brownian drift. If D and d are in cm and s is in cm sec$^{-\frac{1}{2}}$, then t will be in seconds. The value of k is between about 1 and 10 for all practical purposes.

If the sample is allowed to flow past the active region so as to move through the length of the active region for a period equal to the static incubation time, then, from equation (3), we find $$v = L/t = 4Ls^2/k(D-d)^2 \qquad (4)$$

where v is the flow velocity.

Combining equations (2) and (3), we find the volume scavenged per unit incubation time, V/t, to be $$V/t = pi\, L\, s^2\, (D+d)/k(D-d) \qquad (5)$$

Equation 5 defines the actual effective sample volume flow per unit time. A larger flow rate will not permit completely scavenging the sample, while a smaller volume flow rate will result in the sample being opposite the active region for a longer than the necessary time.

It may be seen from equation (5) that the value of V/t may be maximized by increasing the length of the active region, and by appropriately adjusting the difference between D and d to be as small as possible. It should be noted however that it is not necessary to constrict physically the capillary diameter. The volume due to additional diameter will then not be sampled, but waste of some sample is usually tolerable and preferable to having to build apparatus with extremely small tolerance requirements.

A large capillary volume may be used with a sample flow velocity larger than that given by equation (4) so as to produce an effective capillary diameter, $D_{eff}$, given by $$D_{eff} = d + s\, (L/kv)^{\frac{1}{2}} \qquad (6)$$

In such an arrangement, k will be smaller, and therefore the optimal volume to time ratio, V/t, will be larger because of the scavenging of sample outside of the effective diameter, $D_{eff}$, as well as the lack of a need to wait for the complete scavenging of the sample.

As an example, for D=4d, (D+d)/(D−d)=1.66, while for D=1.1 d, (D+d)/(D−d)=21. The latter is a 12.6 fold improvement.

It will also be understood that fiber 12 and tube 14 might be of other than right circular cylindrical shape, and that, for instance, they might be a pair of parallel plates with a capillary spacing therebetween.

Since these and certain other changes may be made in the above apparatus and method without departing from the scope of the invention herein involved, it is intended that all matter contained in the above description or shown in the accompanying drawing shall be interpreted in an illustrative and not a limiting sense.

What is claimed is:

1. In a method for performing assays involving measurement of fluorescence excited in a fluid sample by an evanescent wave at a surface region of a totally internally reflecting substrate, the improvement comprising:
    exciting said fluorescence while flowing through an enclosure of fixed dimensions bounded in part by said region, a sufficient volume of said sample to maintain said enclosure filled with flowing sample.

2. The improvement according to claim 1 wherein said surface region is coated with a coating having a plurality of sites, each site being capable of having attached thereto a selected moiety of a chemical complex, said complex being capable of fluorescing when excited by said evanescent wave, including the step of maintaining the rate (v) of flow of said volume of sample at least at L/t;
    where L is the length of said region, measured in the direction of the flow of said sample past said region; and
    t is the time required for said coating to scavenge a static volume of said sample filling said enclosure.

3. The improvement as defined in claim 1 wherein at least the minimum cross-section dimension of said enclosure is of capillary dimensions with respect to said fluid sample.

4. In apparatus for assaying a fluid sample, said apparatus including a totally internally reflecting substrate transmissive to radiation capable of exciting fluorescence in fluorescent material disposed at least on a portion of the surface of said substrate, said substrate also being transmissive to said fluorescence, and means spaced from at least said portion of said surface of said substrate so as to define an enclosure bounded in part by said portion, the improvement comprising:
    means for flowing substantially continuously said sample over at least said portion of said surface and in sufficient volume to fill said enclosure, while exciting said fluorescence.

5. In apparatus as defined in claim 4 wherein said substrate is an optical fiber.

6. In apparatus as defined in claim 5 wherein said enclosure is a tube coaxially spaced apart from and surrounding said fiber.

7. In apparatus as defined in claim 6 wherein the interspace between said tube and fiber is of capillary dimensions.

8. In apparatus as defined in claim 4 including a fluorimeter disposed for measuring fluorescence excited by said evanescent wave.

9. In apparatus as defined in claim 4 including means for controlling at least the rate of flow of said sample.

10. In apparatus as defined in claim 9 wherein said means for controlling said rate of flow comprises fluid pumping means.

11. In apparatus as defined in claim 9 wherein said portion is coated with a coating having a plurality of sites, each of said sites being capable of having attached thereto a selected moiety of a chemical complex capable of fluorescing when excited by said radiation, and
wherein said means for controlling said flow rate provides a rate (v) of flow of said volume substantially of L/t;

where L is the length, measured in the direction of the flow of said sample, of said region, and
t is the time required for said material to scavenge a static volume of said sample filling said enclosure.

* * * * *